(12) United States Patent
Nakajima et al.

(10) Patent No.: US 10,420,269 B2
(45) Date of Patent: Sep. 17, 2019

(54) MOUNTING INSPECTION DEVICE

(71) Applicant: FUJI CORPORATION, Chiryu (JP)

(72) Inventors: Mikio Nakajima, Toyokawa (JP);
Mitsutaka Inagaki, Anjo (JP)

(73) Assignee: FUJI CORPORATION, Chiryu (JP)

( * ) Notice: Subject to any disclaimer, the term of this patent is extended or adjusted under 35 U.S.C. 154(b) by 178 days.

(21) Appl. No.: 15/021,042

(22) PCT Filed: Sep. 17, 2013

(86) PCT No.: PCT/JP2013/075012
§ 371 (c)(1),
(2) Date: Mar. 10, 2016

(87) PCT Pub. No.: WO2015/040667
PCT Pub. Date: Mar. 26, 2015

(65) Prior Publication Data
US 2016/0227683 A1    Aug. 4, 2016

(51) Int. Cl.
*H05K 13/08* (2006.01)
*G01N 21/956* (2006.01)

(52) U.S. Cl.
CPC ......... *H05K 13/08* (2013.01); *H05K 13/0815* (2018.08); *G01N 2021/95638* (2013.01)

(58) Field of Classification Search
CPC ..................... H05K 13/08; G01N 2021/95638
USPC .......................................................... 348/87
See application file for complete search history.

(56) References Cited

U.S. PATENT DOCUMENTS

| | | | |
|---|---|---|---|
| 2009/0000110 A1* | 1/2009 | Maenishi | ............... H05K 13/08 |
| | | | 29/743 |
| 2010/0152877 A1* | 6/2010 | Maenishi | ........... H05K 13/0413 |
| | | | 700/108 |

FOREIGN PATENT DOCUMENTS

| JP | 6-201603 A | 7/1994 |
|---|---|---|
| JP | 2002-181731 | 6/2002 |
| JP | 2002-368500 A | 12/2002 |
| JP | 2003-004659 A | 1/2003 |
| JP | 2004-301574 A | 10/2004 |
| JP | 2010-8149 A | 1/2010 |
| JP | 2010008149 A * | 1/2010 |
| JP | 2010008149 A * | 1/2010 |

OTHER PUBLICATIONS

Extended European Search Report dated Aug. 2, 2016 in Patent Application No. 13893900.4.
(Continued)

*Primary Examiner* — Ayman A Abaza
(74) *Attorney, Agent, or Firm* — Oblon, McClelland, Maier & Neustadt, L.L.P.

(57) ABSTRACT

A mounting inspection device includes a missing component inspection device and a foreign object inspection device. The missing component inspection device is for performing missing component inspection of components mounted on a printed circuit board. The foreign object inspection device is for performing foreign object inspection in which foreign objects on a printed circuit board are inspected with regard to the printed circuit board on which a missing component is detected, based on results of the missing component inspection carried out by the missing component inspection device.

5 Claims, 7 Drawing Sheets

(56) References Cited

OTHER PUBLICATIONS

International Search Report dated Jan. 14, 2014 in PCT/JP13/75012 Filed Sep. 17, 2013.
Office Action dated May 8, 2018 in Japanese Patent Application No. 2015-537442 (with English translation).

* cited by examiner

MOUNTING INSPECTION DEVICE

TECHNICAL FIELD

The present disclosure relates to amounting inspection device.

BACKGROUND ART

In the related art, as a mounting inspection device, there is known a device which performs inspection of a missing component of the mounting or the like after soldering and mounting an electronic component to electrode pads of a printed circuit board. For example, a missing component inspection device described in PTL 1 first images a bare printed circuit board on which no electronic components are mounted and a mounted printed circuit board on which electronic components are mounted using a camera, and obtains luminance data of each. Next, the missing component inspection device performs the algorithm selection and the threshold calculation of the missing component inspection based on the difference values of the luminance data of each. The missing component inspection device performs the missing component inspection based on the calculated threshold and the luminance information of the installed printed circuit board using the selected algorithm. In this manner, the missing component inspection device can more reliably determine whether there is a missing component.

CITATION LIST

Patent Literature

PTL 1: JP-A-6-201603

SUMMARY

However, in the mounting inspection device described in PTL 1, although the determination of whether there is a missing component is performed, no consideration is given to where the electronic component which is a missing component is located. For example, when there is a missing component due to an electronic component falling onto the printed circuit board while the electronic component is conveyed to the mounting position or the like, when the process flow continues to subsequent processes with the missing electronic component left on the printed circuit board, there is a case in which the printed circuit board becomes a faulty printed circuit board.

The present disclosure was made in light of this problem, and the main object of the present disclosure is to further suppress the occurrence of a printed circuit board on which a missing component is detected becoming a faulty printed circuit board.

Solution to Problem

A mounting inspection device of the present disclosure includes missing component inspection means for performing missing component inspection of components mounted on a printed circuit board, and foreign object inspection means for performing foreign object inspection in which foreign objects on a printed circuit board are inspected with regard to a printed circuit board on which a missing component is detected, based on results of the missing component inspection carried out by the missing component inspection means.

The mounting inspection device performs foreign object inspection on a printed circuit board for a printed circuit board on which a missing component of the components (electronic components and the like) which are mounted thereon is detected, based on results of the missing component inspection. By doing so, when the component which is a missing component is present on the printed circuit board, it is possible to detect the component as a foreign object. Therefore, it is possible to suppress the occurrence of the component which is a missing component being left on the printed circuit board, and it is possible to further suppress the occurrence of the printed circuit board on which the missing component is detected becoming a faulty board. In this case, the foreign object inspection means may not perform the foreign object inspection on a printed circuit board on which the missing component is not detected by the missing component inspection. By doing so, it is possible to more efficiently perform the inspection of the printed circuit board.

In the mounting inspection device of the present disclosure, the foreign object inspection means may acquire missing component position information which is information relating to a position in which the missing component is detected in the printed circuit board, and may preferentially perform the foreign object inspection on a periphery of the position which is specified by the missing component position information in the printed circuit board. There is a relatively strong possibility that the component which is a missing component is present in the periphery of the position in which the missing component is detected, that is, the correct position of the component. Therefore, by preferentially performing the foreign object inspection on the periphery of position in which the missing component is detected, it is possible to more efficiently detect the component which is a missing component.

In the mounting inspection device of the present disclosure, the foreign object inspection means may acquire missing component conveying information which is information relating to a conveyance path over the printed circuit board when mounting a component which is the detected missing component, and may preferentially perform the foreign object inspection on a region which is specified by the missing component conveying information in the printed circuit board. In a case such as one in which the component which is a missing component falls during the conveying, there is a relatively strong possibility that the missing component is present in the conveyance path to the position in which the missing component is detected, that is, in the conveyance path to the correct position. Therefore, by preferentially performing the foreign object inspection on the region of the conveyance path in the printed circuit board, it is possible to more efficiently detect the component which is a missing component.

In the mounting inspection device of the present disclosure, the foreign object inspection means may perform the foreign object inspection based on image processing, acquire missing component size information which is information relating to a size of a component which is the detected missing component, and, based on the acquired missing component size information, perform the foreign object inspection, ignoring foreign objects which are smaller than the component which is the missing component among the foreign objects which are detected based on the image processing. By doing so, it is possible to more efficiently detect the component which is a missing component. In this case, when there is a plurality of components which are the detected missing components, based on the missing component size information of the smallest component among the components which are the missing components, the foreign object inspection means may perform the foreign object inspection, ignoring foreign objects which are smaller than the smallest component among the foreign objects which are detected based on the image processing. By doing so, when there is a plurality of the components which are missing components, it is possible to more efficiently detect the component which is a missing component.

In the mounting inspection device of the present disclosure, the printed circuit board may be a multiple printed circuit board including a plurality of child boards, and, for the multiple printed circuit board on which the missing component is detected by the missing component inspection means, the foreign object inspection means may also perform the foreign object inspection on one or more child boards other than the child board on which the missing component is detected in the multiple printed circuit board. By doing so, even when there is a component which is a missing component on a child board other than the child board on which the missing component is detected, it is possible to detect the component.

Note that, the mounting inspection device of the present disclosure may be provided with notification means for performing notification of presence of a foreign object when a foreign object is detected in the foreign object inspection. In this case, when the foreign object inspection means detects the foreign object, the foreign object inspection means may specify the position of the foreign object on the printed circuit board, and the notification means may perform notification of the position of the specified foreign object. By doing so, it is possible to efficiently remove the foreign object from the printed circuit board based on the notified position.

The mounting inspection device of the present disclosure may include reference image acquisition means for acquiring one or more of pre-mounting reference image data which express a state before mounting of a printed circuit board and post-mounting reference image data which expresses a correct state after the mounting of the printed circuit board, and captured image acquisition means for acquiring captured image data by capturing an image of the printed circuit board after the mounting, in which the foreign object inspection means may inspect a foreign object on the printed circuit board based on a comparison between one or more of the pre-mounting reference image data and the post-mounting reference image data, and the captured image data.

DETAILED DESCRIPTION

Figure 1:
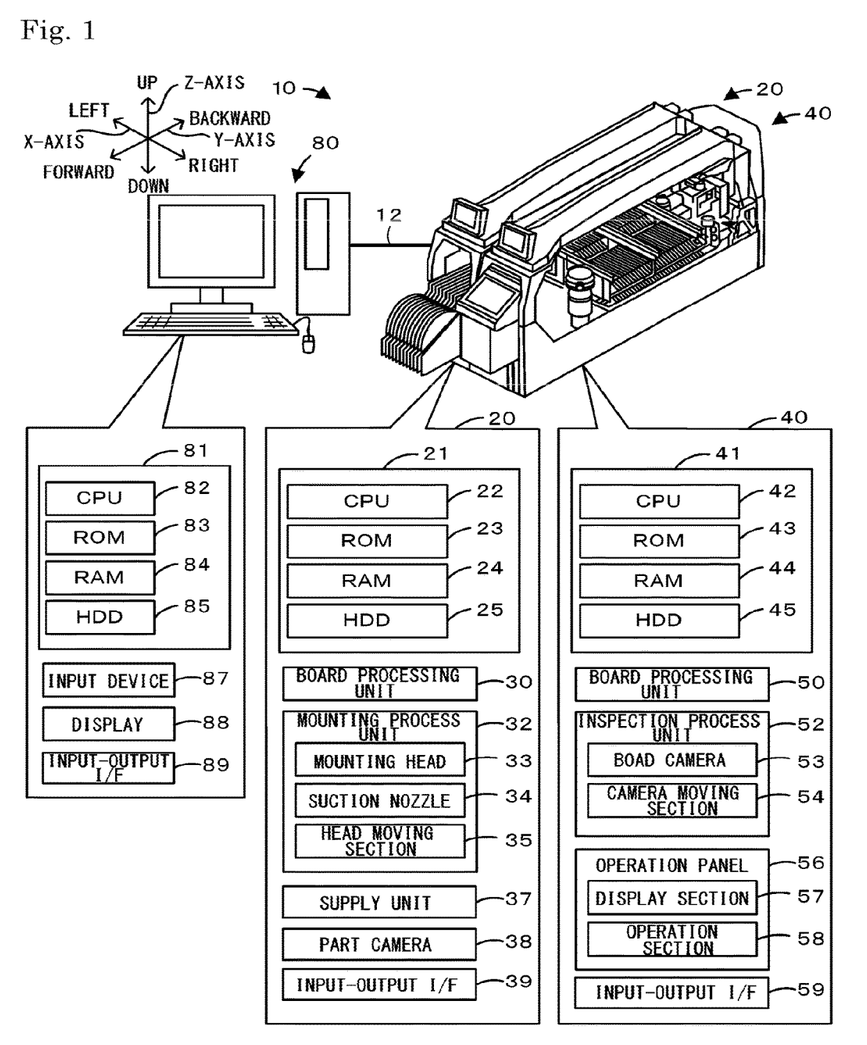
FIG. 1 is a configuration diagram schematically illustrating the configuration of a component mounting system 10.

Next, description will be given of a mode for carrying out the present disclosure using the drawings. FIG. 1 is a configuration diagram schematically illustrating the configuration of a component mounting system 10 which is an embodiment of the present disclosure. The component mounting system 10 is provided with a plurality of mounting process devices 20, each of which is connected to a LAN 12 serving as a network and mounts one or more electronic components (a component P) on the printed circuit board S (for the component P and the printed circuit board S, refer to FIG. 4 described later), one or more mounting inspection devices 40, each of which is connected to the LAN 12 and inspects amounting state of the component P, and a management computer 80 which is connected to the LAN 12 and manages information relating to the processes in each of the mounting process devices 20 and each of the mounting inspection devices 40. A plurality of the mounting process devices 20 in which reels which store the various components P are installed are connected to the component mounting system 10, and the component mounting system 10 is configured as amounting line which conveys the printed circuit boards S and mounts the components P. In FIG. 1, the component mounting system 10 is provided with a single mounting process device 20 and a single mounting inspection device 40; however, further mounting process devices 20 and mounting inspection devices 40 may be provided. Note that, in the present embodiment, the left-right directions (an X axis), the forward-backward directions (a Y axis), and the up-down directions (a Z axis) are as illustrated in FIG. 1. Note that, "mount" includes disposing, installing, inserting, joining, suction, or the like of the component P on the printed circuit board S.

The mounting process device 20 is provided with amounting control unit 21 which executes various controls, a board processing unit 30 which executes conveying and fixing of the printed circuit board S, and a mounting process unit 32 which executes a process of disposing the components P on the printed circuit board S. The mounting process device 20 is provided with a supply unit 37 which supplies the component P which is stored in a reel or on a tray to a predetermined pickup position, apart camera 38 which images a sucked component P, and an input-output interface (I/F) 39 which performs communication with devices which are connected to the LAN 12.

The board processing unit 30 is provided with a board conveyance section which conveys the printed circuit board S to a predetermined mounting position at which the component P is disposed, and a board holding section which fixes the conveyed printed circuit board S in the mounting position. For example, the board conveyance section is configured as a device which conveys the printed circuit board S using a belt conveyor, and is provided with a guide member which is provided on each of a pair of side frames, a conveyor belt which is provided on each of the pair of side frames, and a belt revolution device which causes the conveyor belt to drive in a revolving manner. The board holding section is disposed at every predetermined mounting position, and, for example, is provided with a support device which supports the printed circuit board S from below, and a clamp device which clamps the edge portions of the printed circuit board S.

The mounting process unit 32 is provided with a mounting head 33, a suction nozzle 34 which is mounted to the mounting head 33 via a nozzle holding body, and a head moving section 35 which moves the mounting head 33 in the X and Y directions. A Z-axis motor which is not depicted in the drawings is embedded in the mounting head 33, and the height of the suction nozzle 34 which is attached to a Z-axis direction ball screw which is not depicted in the drawings is adjusted using the Z-axis motor. Note that, the X and Y directions refer to the directions of two axes which orthogonally intersect within a horizontal plane, and the Z axis refers to the axis of a perpendicular direction. The suction nozzle 34 sucks the component P to the nozzle tip, releases the component P which is sucked by the nozzle tip, and the like using pressure. Piping which is not depicted in the drawings is connected to the suction nozzle 34, a negative pressure is supplied to the nozzle tip via the piping during the suction of the component P to the nozzle tip, and a positive pressure is supplied to the nozzle tip via the piping when releasing the component P which is sucked at the nozzle tip. Note that, it is possible to exchange the suction nozzle 34 for one which matches the size and shape of the component P. The head moving section 35 is capable of moving in the X directions due to an X direction slider which is not depicted in the drawings, and is capable of moving in the Y directions due to a Y direction slider which is not depicted in the drawings. The mounting head 33 moves in the X and Y directions together with the movement of the head moving section 35 in the X and Y directions. Note that, each of the sliders is driven by a corresponding drive motor.

The supply unit 37 is provided with a reel supply section which supplies the component P from the reel. The reel supply section is provided with a mounting section which mounts the reel, a tape feeder section which feeds the tape out from the wound reel to the suction position, and a cutting section which cuts and discards the tape from which the component P has been taken. According to the reel supply section, the component P which is stored in the reel is fed out to the pickup position at which suction is performed by the suction nozzle 34. Note that, in the mounting process device 20, in addition to the reel supply section, it is possible to exchange the reel supply section for a tray supply unit which stores a plurality of trays on which a plurality of the components P is placed. The tray supply section is provided with a mounting section which mounts a magazine cassette in which a plurality of trays is stored, and a tray moving section which feeds out a desired tray from the magazine cassette which is mounted to the mounting section.

The mounting control unit 21 is configured as a microprocessor centered on a CPU 22, is provided with a ROM 23 which stores process programs, a RAM 24 which is used as a working region, an HDD 25 which stores various data, and the like, and these are connected via a bus. The mounting control unit 21 performs input and output of signals and information with the board processing unit 30, the mounting process unit 32, the supply unit 37, and the management computer 80 via the input-output interface 39. The mounting control unit 21 outputs an imaging signal to the part camera 38, receives input of an image signal from the part camera 38, and the like via the input-output interface 39. The mounting control unit 21 which is configured in this manner executes a process which causes the suction nozzle 34 to suck each of the components P, moves the mounting head 33 using the head moving section 35, and mounts each of the components P on the printed circuit board S based on the mounting condition information containing the conditions relating to the mounting of each of the components P. The mounting condition information is managed by the management computer 80.

The mounting inspection device 40 is provided with an inspection control unit 41 which executes various controls, the board processing unit 50 which executes the conveying and the fixing of the printed circuit board S on which the components P are mounted, an inspection process unit 52 which images the printed circuit board S during the inspection of the printed circuit board S, an operation panel 56 on which a display screen is displayed and with which a worker can perform various input operations, and an input-output interface (I/F) 59 which performs communication with devices connected to the LAN 12.

The board processing unit 50 is provided with a board conveyance section which conveys the printed circuit board S to a predetermined inspection position, and a board holding section which fixes the conveyed printed circuit board in the inspection position. Note that, since the configuration of the board processing unit 50 is the same as that of the board processing unit 30, description thereof will be omitted.

The inspection process unit 52 is provided with a board camera 53 which images the printed circuit board S and acquires captured images including images of the board ID (an ID expressing the model of the product class of the printed circuit board S), the components P, and the like on the printed circuit board S, and a camera moving section 54 which moves the board camera 53 in the X and Y directions to move the printed circuit board S to a position at which it is possible to perform the imaging. The board camera 53 is provided with a lighting section which illuminates the printed circuit board S with light, imaging elements which generate charges by receiving light and output the generated charges, and an image processing section which generates captured image data including the captured image based on the output charges. The camera moving section 54 is capable of moving in the X directions due to an X direction slider which is not depicted in the drawings, and is capable of moving in the Y directions due to a Y direction slider which is not depicted in the drawings. The board camera 53 moves in the X and Y directions together with the movement of the camera moving section 54 in the X and Y directions. Note that, each of the sliders is driven by a corresponding drive motor.

The operation panel 56 is provided with a display section 57 which displays a screen, and an operation section 58 which receives an input operation from a worker. The display section 57 is configured as a liquid crystal display, and displays, on a screen, the operation state and the setting state of the mounting inspection device 40. The operation section 58 is provided with cursor keys which move a cursor up, down, left, or right, a cancel key which cancels the input, a decision key which decides the selected content, and the like, and is configured to be capable of receiving the key input of an instruction of the worker.

The inspection control unit 41 is configured as a microprocessor centered on a CPU 42, is provided with a ROM 43 which stores process programs, a RAM 44 which is used as a working region, an HDD 45 which stores various data, and the like, and these are connected via a bus. The inspection control unit 41 outputs control signals to the board processing unit 50 and the inspection process unit 52, outputs display data to the operation panel 56, transmits information to the management computer 80, and the like via the input-output interface 59. The inspection control unit 41 receives input of signals from the board processing unit 50, acquires the captured image data which is imaged by the board camera 53, receives input of data which is input to the operation panel 56 and the like, receives information from the management computer 80, and the like via the input-output interface 59.

Figure 2:
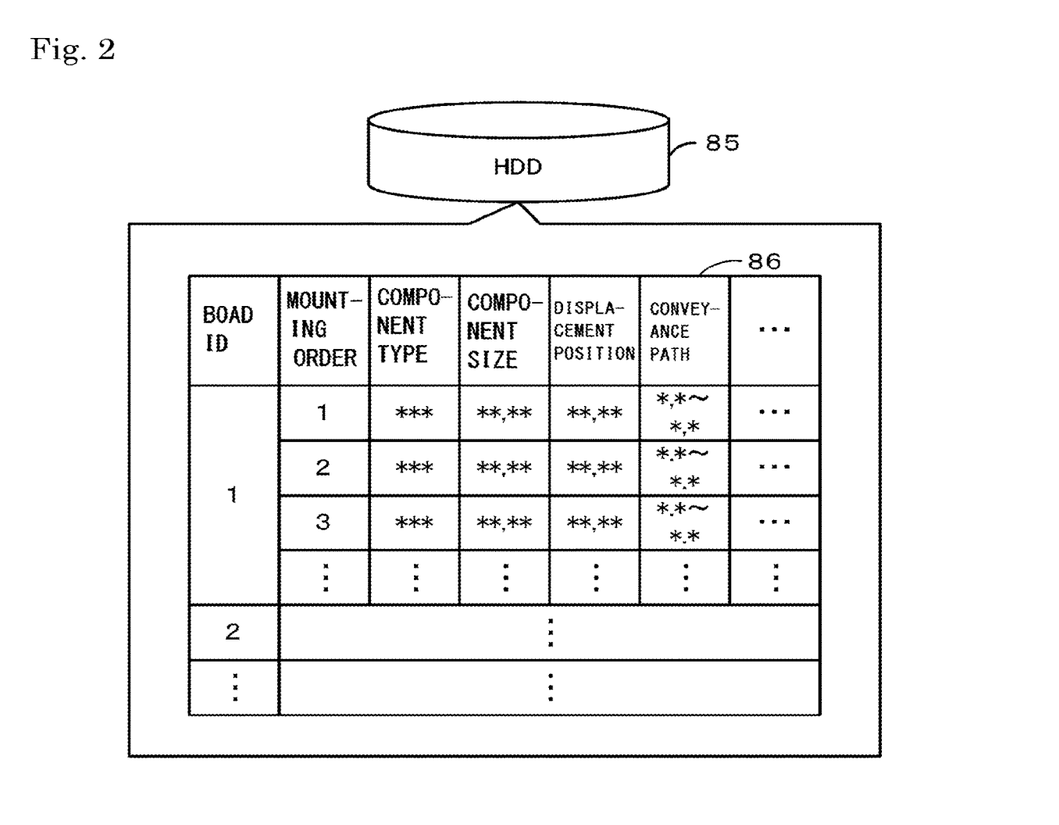
FIG. 2 is an explanatory diagram of mounting condition information 86.

The management computer 80 is provided with a control device 81, and is a computer which manages the information of the plurality of mounting process devices 20 and the plurality of mounting inspection devices 40. The control device 81 is configured as a microprocessor centered on a CPU 82, is provided with a ROM 83 which stores process programs, a RAM 84 which is used as a working region, an HDD 85 which stores various data, and the like, and these are connected via a bus. The management computer 80 is provided with an input device 87 such as a keyboard and a mouse with which the worker inputs various instructions, a display 88 which displays various information, and an input-output interface 89 for performing transactions of electrical signals with external devices. The mounting condition information 86 which is used in the mounting in the mounting process device 20 and the inspection in the mounting inspection device 40, inspection condition information used in the inspection in the mounting inspection device 40, and the like are stored in the HDD 85 of the management computer 80. FIG. 2 is an explanatory diagram of the mounting condition information 86. For example, the mounting condition information 86 includes information such as the mounting order of the components P, the component types, the component sizes, the disposition positions on the printed circuit board S, and the conveyance paths above the printed circuit board S during the mounting, and these items of information are associated with the board IDs of the printed circuit boards S on which to perform the mounting. Note that, the information of the component size is information expressing the vertical and horizontal lengths (the lengths in the X and Y directions during the mounting) of the component P, for example. The information of the disposition position is information expressing the XY coordinates of the center of the component P, for example. The information of the conveyance path is information expressing the XY coordinates of a plurality of points on the conveyance path of the component P above the printed circuit board S when the mounting head 33 moves the component P to the disposition position, for example. Although omitted from the drawings, the inspection conditions such as the imaging conditions and the imaging region (the missing component inspection region) of the inspection process unit 52, and the movement conditions under which the board camera 53 is moved are associated with the board ID of the printed circuit board S in the inspection condition information. Pre-mounting reference image data including an image in which the state of the printed circuit board S before the mounting is imaged, and post-mounting reference image data including an image in which the correct state of the detection target printed circuit board S after the mounting is imaged are associated with the board ID of the printed circuit board S and stored in the HDD 85. The pre-mounting reference image data and the post-mounting reference image data are data of images which are obtained by imaging the printed circuit board S in advance using the board camera 53, for example.

Figure 3:
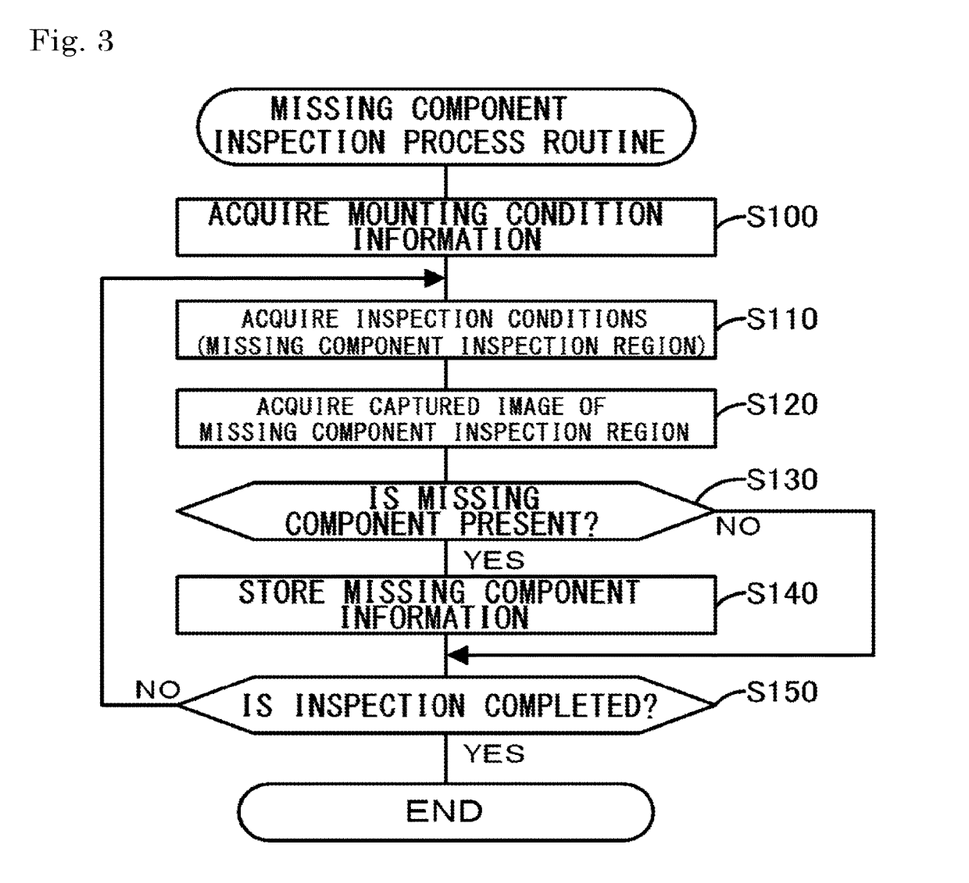
FIG. 3 is a flowchart illustrating an example of a missing component inspection process routine.

Next, description will be given of the operations of the mounting inspection device 40 of the present embodiment which is configured in this manner, in particular, the process of executing the missing component inspection and the foreign object inspection in relation to the printed circuit board S for which the mounting of the components P by the mounting process device 20 is completed. First, description will be given of the missing component inspection process which is performed by the mounting inspection device 40. FIG. 3 is a flowchart illustrating an example of a missing component inspection process routine which is executed by the CPU 42 of the inspection control unit 41. This routine is stored in the HDD 45 of the mounting inspection device 40 and is executed when the printed circuit board S for which the mounting process in the mounting process device 20 is completed is conveyed to the mounting inspection device 40.

Figure 4:
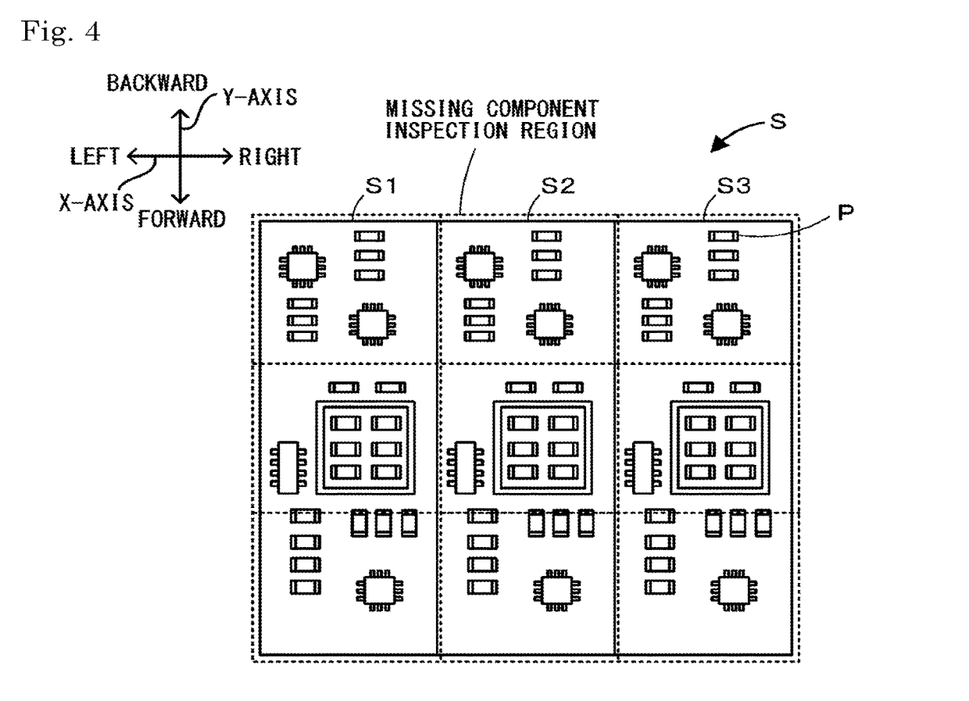
FIG. 4 is an explanatory diagram illustrating a relationship between a printed circuit board S and missing component inspection regions.

When the routine is started, the CPU 42 of the mounting inspection device 40 first acquires the mounting condition information 86 from the management computer 80 and stores the mounting condition information 86 in the HDD 45 (step S100). Next, the CPU 42 reads the inspection condition information from the management computer 80 and acquires the inspection conditions (the missing component inspection region and the like) (step S110). Note that, the size and number of missing component inspection regions (the imaging region) are predetermined based on the size of the printed circuit board S, the size of the range which the board camera 53 is capable of imaging, and the like. FIG. 4 is an explanatory diagram illustrating the relationship between the printed circuit board S and the missing component inspection regions. In FIG. 4, the missing component inspection regions are illustrated as regions surrounded by dashed-line boxes. In the present embodiment, as illustrated, the printed circuit board S is a multiple printed circuit board which includes a plurality of child boards S1 to S3 lined up from the left to the right. Each individual range obtained by dividing each of the child boards S1 to S3 into three (the printed circuit board S is divided into nine) in the forward-backward directions is used as a missing component inspection region. In step S100, information such as the XY coordinates of a single uninspected missing component inspection region among the plurality of missing component inspection regions is acquired according to a predetermined order (for example, the order from the rear left to the front right).

Next, the CPU 42 controls the camera moving section 54 based on the inspection conditions acquired in step S110, moves the board camera 53 to a position at which it is possible to image the missing component inspection region acquired in step S110, controls the board camera 53 to image the missing component inspection region on the printed circuit board S, and acquires a captured image (step S120). Next, the CPU 42 determines whether there is a missing component among the components P which are mounted in the missing component inspection region (step S130). The determination of whether there is a missing component by the CPU 42 can be performed by comparing the captured image data which is acquired in step S120 and the post-mounting reference image data which is stored in the HDD 85 of the management computer 80. Note that, the post-mounting reference image data is acquired from the management computer 80 by the CPU 42. The CPU 42 specifies the regions in which the components P should be present within the missing component inspection region and performs a comparison on the images of those regions between the captured image data and the post-mounting reference image data. When a plurality of the components P are present within the missing component inspection region, the comparison is performed for each of the regions in which each of the components P should be present. The region in which the component P should be present is specified by the CPU 42 by reading information such as the disposition position and the component size of the component P from the mounting condition information 86.

In step S130, when the CPU 42 determines that one or more of the components P are a missing component, the CPU 42 stores information with which it is possible to specify the component P which is determined to be a missing component in the HDD 45 as missing component information (step S140). In the present embodiment, the mounting order of the component P which is determined to be the missing component and the board ID to which the component P is mounted are specified based on the mounting condition information 86, and these items of information are stored as missing component information.

After step S140, or, after the CPU 42 determines that there are no missing components in step S130, the CPU 42 determines whether the missing component inspection is completed, that is, whether the inspection of whether there is a missing component has been performed for all of the plurality of missing component inspection regions described above (step S150). When there is an uninspected missing component inspection region, the CPU 42 executes the processes of step S110 onward. In other words, the CPU 42 reads the inspection information including information of the next missing component inspection region and the like, performs the imaging of the missing component inspection region, inspects whether there is a missing component, and stores missing component information if there is a missing component. When the CPU 42 determines that the missing component inspection is completed in step S150, the missing component inspection process routine ends. In this manner, the CPU 42 inspects for the missing component in the missing component inspection regions using image processing based on the captured image data and the post-mounting reference image data, and performs the missing component inspection for all of the components P on the printed circuit board S by repeating this.

Figure 5:
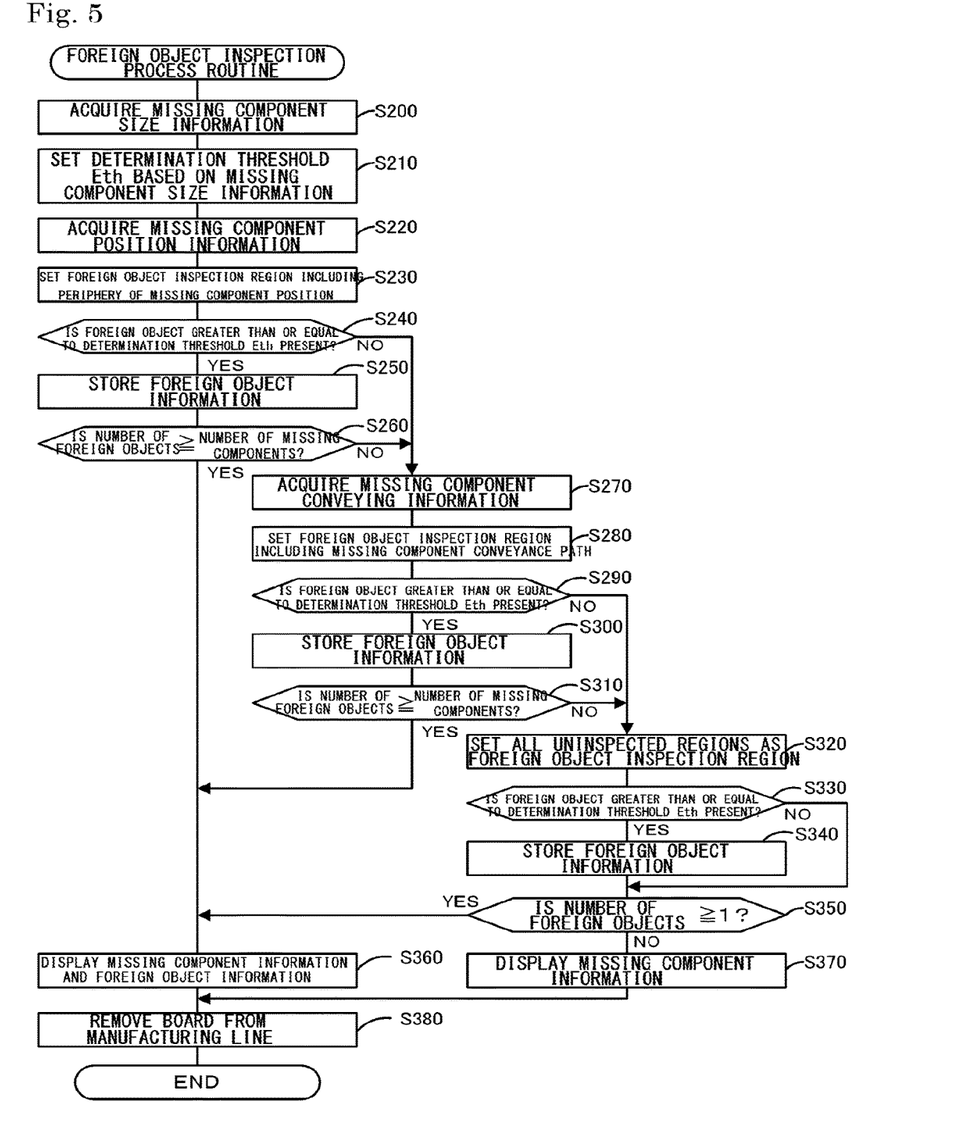
FIG. 5 is a flowchart illustrating an example of a foreign object inspection process routine.

Next, description will be given of the foreign object inspection process which is performed by the mounting inspection device 40. FIG. 5 is a flowchart illustrating an example of a foreign object inspection process routine which is executed by the CPU 42 of the inspection control unit 41. This routine is stored in the HDD 45 of the mounting inspection device 40 and is executed, by the missing component inspection process, on the printed circuit board S for which there are one or more items of missing component information stored in the HDD 45. In other words, the foreign object inspection process is executed on the printed circuit board S on which the missing component is detected, based on the results of the missing component inspection process. The foreign object inspection process is not performed on the printed circuit board S on which not even one missing component is detected in the missing component inspection process.

When the routine is started, the CPU 42 of the mounting inspection device 40 first acquires the missing component size information which is information relating to the size of the component P which is determined to be a missing component in the missing component inspection process (step S200). In the present embodiment, the CPU 42 specifies the component size of the component P which is determined to be a missing component based on the mounting condition information 86 and the missing component information which are stored in the HDD 45 in the missing component inspection process, and acquires the specified component size as the missing component size information. Note that, when there is a plurality of the components P which are determined to be missing components, the CPU 42 acquires each item of missing component size information of each of the components P. Next, the CPU 42 sets a determination threshold Eth for determining a foreign object based on the missing component size information (step S210). In the present embodiment, the determination threshold Eth is set as a value obtained by converting the area on the printed circuit board S occupied by the component P which is determined to be a missing component into a number of pixels and adding a margin thereto (for example, a value obtained by multiplying the converted value by 0.9 or by subtracting a predetermined value from the converted value). Note that, when there is a plurality of the components P which are determined to be missing components, the CPU 42 sets the determination threshold Eth based on the component P which occupies the smallest area on the printed circuit board S among the plurality of components P.

Figure 6:
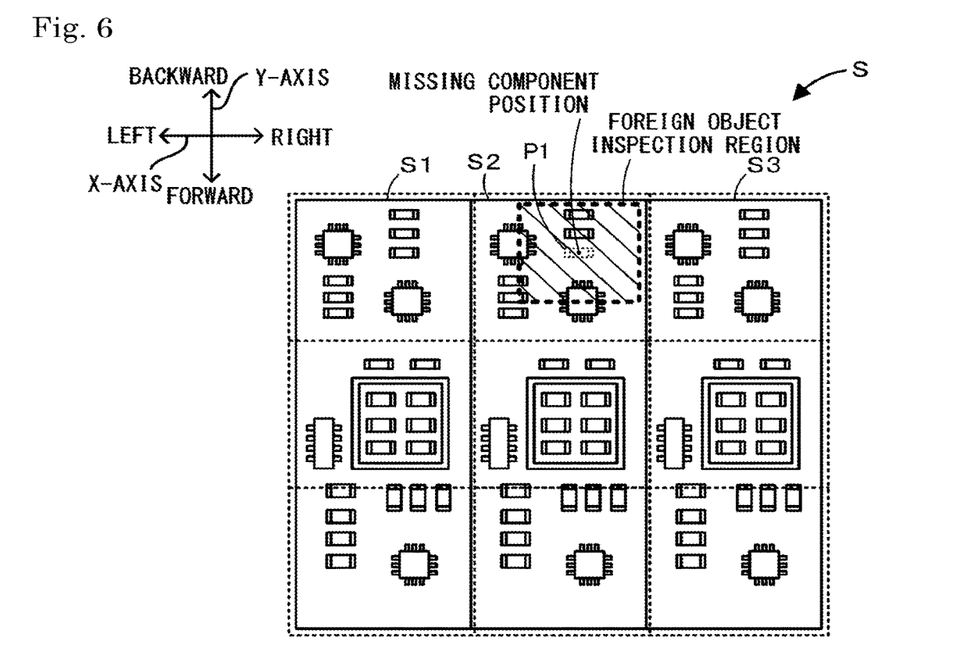
FIG. 6 is an explanatory diagram illustrating a situation in which a foreign object inspection region including a periphery of a missing component position is set.

Next, the CPU 42 acquires missing component position information which is information relating to the position on the printed circuit board S in which the missing component is detected (step S220). In the present embodiment, the CPU 42 specifies the disposition position of the component P which is determined to be a missing component based on the mounting condition information 86 and the missing component information which are stored in the HDD 45 in the missing component inspection process, and acquires the specified disposition position as the missing component position information. Note that, when there is a plurality of the components P which are determined to be missing components, the CPU 42 acquires each item of missing component position information of each of the components P. Next, the CPU 42 sets the foreign object inspection region including the periphery of a missing component position on the printed circuit board S based on the acquired missing component position information (step S230). FIG. 6 is an explanatory diagram illustrating a situation in which a foreign object inspection region including a periphery of a missing component position is set. FIG. 6 illustrates the foreign object inspection region when it is determined that a component P1 on a child board S2 is a missing component. As illustrated, the CPU 42 sets a rectangular region centered on the missing component position, which is the disposition position of the component P1 (in the present embodiment, the center position of the component P1), as the foreign object inspection region. Note that, the size of the rectangular region in the X and Y directions may be a fixed value, and, for example, may be a variable value which is calculated based on the missing component size information such that the bigger the component size of the component P1, the bigger the foreign object inspection region. The shape of the foreign object inspection region is not limited to being rectangular, and, for example, may be circular. Note that, in FIG. 6, although the foreign object inspection region based on the component P1 includes only the child board S2 for which the missing component of the component P1 is detected, when the rectangular region centered on the component P1 includes a region of a portion of the child boards other than the child board S2, it is possible to include the regions other than the child board S2 in the foreign object inspection region. When there is a plurality of the components P which are determined to be missing components, the CPU 42 sets each foreign object inspection region for each of the components P. In other words, the CPU 42 sets a plurality of foreign object inspection regions.

Next, the CPU 42 determines whether there is a foreign object of a size greater than or equal to the determination threshold Eth in the foreign object inspection region which is set in step S230 (step S240). The determination of whether there is a foreign object by the CPU 42 is performed in the following manner, for example. A comparison of the captured image data which is acquired in step S120 of the missing component inspection process routine to the pre-mounting reference image data and the post-mounting reference image data which are stored in the HDD 85 of the management computer 80 is performed, one or more pixels which can be treated as being different in the captured image and the reference image are detected in the foreign object inspection region, and the detected pixels are specified as foreign object candidate pixels. The pre-mounting reference image data and the post-mounting reference image data are acquired from the management computer 80 by the CPU 42. When specifying the foreign object candidate pixels, the CPU 42 performs a comparison based on the pre-mounting reference image data for regions in which a missing component is detected in the foreign object inspection region, and for other regions, the CPU 42 performs a comparison based on the post-mounting reference image data. Note that, the CPU 42 may not perform the comparison for a region in which no missing components are detected in the foreign object inspection region. In this case, it is not necessary to acquire the pre-mounting reference image data. When the foreign object candidate pixels in the foreign object inspection region are specified, the CPU treats the foreign object candidate pixels which are continuous in the X directions and the Y directions as a single foreign object candidate, and determines whether there is a foreign object candidate including a number greater than or equal to the determination threshold Eth of the foreign object candidate pixels in the foreign object inspection region. The CPU 42 detects the foreign object candidate including a number greater than or equal to the determination threshold Eth of foreign object candidate pixels as a foreign object. Note that, when there is a plurality of the foreign object candidates including a number greater than or equal to the determination threshold Eth of foreign object candidate pixels, the CPU 42 detects each of a plurality of foreign objects. When a foreign object candidate including pixels of the end portion (the outer circumference) of the foreign object inspection region is present, the CPU 42 may also perform the comparison for the pixels of the periphery of the foreign object inspection region. By doing so, even when the foreign object candidate spans both the inside and the outside of the foreign object inspection region, it is possible to more appropriately determine whether the foreign object candidate is a foreign object by appropriately calculating the size of the foreign object candidate (the number of foreign object candidate pixels). When a plurality of foreign object inspection regions are set, the CPU 42 determines whether there is a foreign object of a size greater than or equal to the determination threshold Eth for each of the foreign object inspection regions. In this manner, the CPU 42 sets the periphery of the missing component position on the printed circuit board S as a foreign object inspection region, and preferentially performs the foreign object inspection on this foreign object inspection region. The CPU 42 performs the foreign object inspection ignoring the foreign objects (the foreign object candidates) which are less than the determination threshold Eth.

When the CPU 42 determines that there are one or more foreign objects instep S240, the CPU 42 stores the information with which it is possible to specify foreign objects as foreign object information in the HDD 45 (step S250). In the present embodiment, the CPU 42 stores the center coordinates of the foreign object in the X and Y directions as foreign object information, which is information which specifies the position of the detected foreign object on the printed circuit board S. Next, the CPU 42 determines whether the number of foreign objects detected in step S240 is greater than or equal to the number of missing components detected in the missing component inspection process (step S260).

After the CPU 42 determines that there are no foreign objects in step S240, or after the CPU 42 determines that the number of foreign objects is less than the number of missing components in step S260, the CPU 42 acquires the missing component conveying information which is information relating to the conveyance path over the printed circuit board S of the component P which is detected as a missing component in the printed circuit board S (step S270). In the present embodiment, the CPU 42 specifies the conveyance path of the component P which is determined to be a missing component based on the mounting condition information 86 and the missing component information which are stored in the HDD 45 in the missing component inspection process, and acquires the specified conveyance path as the missing component conveying information. Note that, when there is a plurality of the components P which are determined to be missing components, the CPU 42 acquires each item of missing component conveying information of each of the components P.

Figure 7:
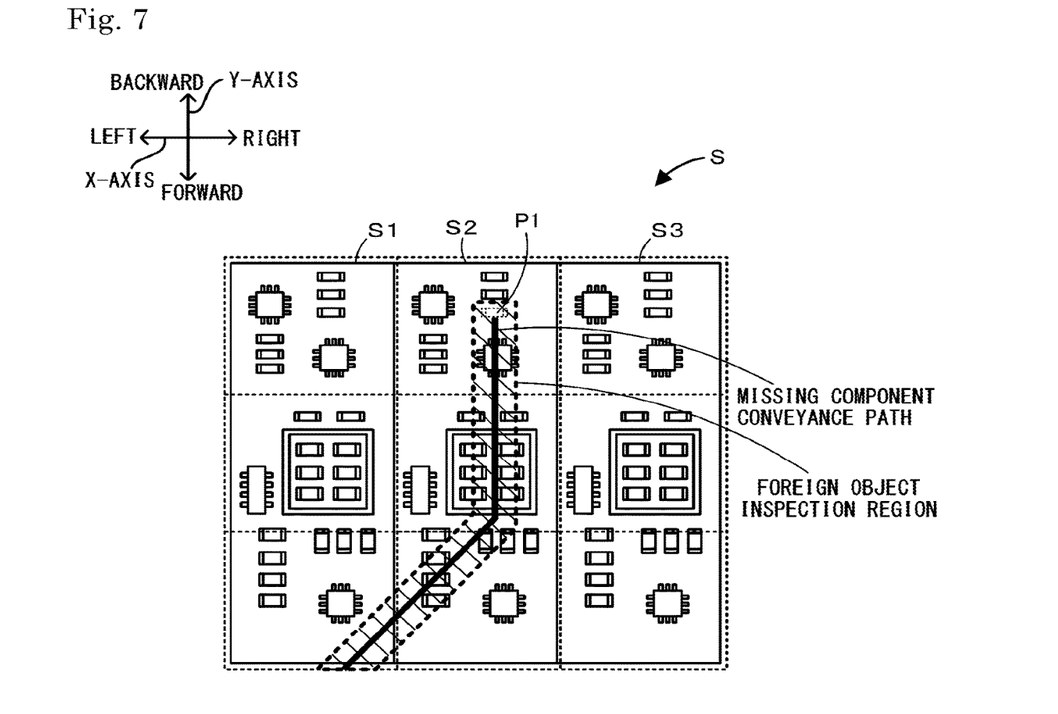
FIG. 7 is an explanatory diagram illustrating a situation in which a foreign object inspection region including a missing component conveyance path is set.

Next, the CPU 42 sets the foreign object inspection region including the missing component conveyance path over the printed circuit board S based on the acquired missing component conveying information (step S280). FIG. 7 is an explanatory diagram illustrating a situation in which a foreign object inspection region including a missing component conveyance path is set. FIG. 7 illustrates the foreign object inspection region when it is determined that the component P1 on the child board S2 is a missing component in the same manner as FIG. 6. As illustrated, the missing component conveyance path which is the conveyance path of the component P1 on the printed circuit board S during the mounting is a bent line shaped path formed by combining a straight line heading from the front end of the printed circuit board S toward the rear right and a straight line toward the rear along the Y direction to the component P1. The CPU 42 sets a region including the missing component conveyance path as the foreign object inspection region. Note that, although the missing component conveyance path is a folded line shape in FIG. 7, the shape is not limited thereto, and may be a straight line shape, a curved line shape, or the like. Note that, for example, the foreign object inspection region may be a region in which the missing component conveyance path is expanded in the X and Y directions by a fixed value, and may be a region expanded in the X and Y directions by a variable value calculated based on the missing component size information such that the bigger the component size of the component P1, the bigger the foreign object inspection region. Note that, as illustrated in FIG. 7, when the printed circuit board S is a multiple printed circuit board, the CPU 42 includes a child board S1 other than the child board S2 in which the missing component is detected in the foreign object inspection region. When there is a plurality of the components P which are determined to be missing components, the CPU 42 sets each foreign object inspection region for each of the components P. In other words, the CPU 42 sets a plurality of foreign object inspection regions. Regarding regions in which the determination of step S240 was already performed such as the regions which are set as foreign object inspection regions in step S230, these regions maybe excluded from the foreign object inspection region which is set in step S280.

Next, the CPU 42 determines whether there is a foreign object of a size greater than or equal to the determination threshold Eth in the foreign object inspection region which is set in step S280 (step S290), and when it is determined that there is one or more of the foreign objects, the foreign object information is stored in the HDD 45 (step S300). The processes of steps S290 and S300 are performed by the CPU 42 in the same manner as the processes of steps S240 and S250. In this manner, the CPU 42 sets a region including the missing component conveyance path in the printed circuit board S as a foreign object inspection region, and preferentially performs the foreign object inspection on this foreign object inspection region. After the CPU 42 performs the processes of step S300, the CPU 42 determines whether the number of foreign objects (the total number) which are detected in step S240 and step S290 is greater than or equal to the number of missing components detected in the missing component inspection process (step S310).

After the CPU 42 determines that there are no foreign objects in step S290, or after the CPU 42 determines that the number of foreign objects is less than the number of missing components in step S310, the CPU 42 sets all of the uninspected foreign object inspection regions, on which the foreign object inspection has not been performed, on the printed circuit board S as the foreign object inspection region (step S320). Note that, in the same manner as in step S280, when the printed circuit board S is a multiple printed circuit board, the CPU 42 includes a child board other than the child board on which the missing component is detected in the foreign object inspection region. Next, the CPU 42 determines whether there is a foreign object of a size greater than or equal to the determination threshold Eth in the foreign object inspection region which is set in step S320 (step S330), and when it is determined that there are one or more of the foreign objects, the foreign object information is stored in the HDD 45 (step S340). The processes of steps S330 and S340 are performed by the CPU 42 in the same manner as the processes of steps S240 and S250. In this manner, when the number of foreign objects detected is not equal to or greater than the number of missing components in the foreign object inspection region for which the foreign object inspection is performed preferentially, the CPU 42 performs the foreign object inspection for all of the uninspected foreign object inspection regions on the printed circuit board S.

After the CPU 42 performs the processes of step S340, or after the CPU 42 determines that there are no foreign objects in step S330, the CPU 42 determines whether the number of foreign objects (the total number) detected in step S240, step S290, and step S330 is greater than or equal to a value 1 (step S350).

After the CPU 42 determines whether the number of foreign objects is greater than or equal to the number of missing components in step S260 and step S310, or after the CPU 42 determines that the number of foreign objects is greater than or equal to a value 1 in step S350, the CPU 42 controls the operation panel 56 to display a predetermined inspection results display screen including the missing component information which is stored in step S140 of the missing component inspection process, and the foreign object information which is stored in one or more of step S250, step S300, and step S340 on the display section 57 (step S360). Accordingly, the worker is notified of information relating to the presence of missing components and foreign objects or relating to the missing components, position information of the foreign objects on the printed circuit board S, and the like.

Meanwhile, after the CPU 42 determines that the number of foreign objects is a value 0 in step S350, the CPU 42 controls the operation panel 56 to display a inspection results display screen including the missing component information which is stored in step S140 of the missing component inspection process on the display section 57 (step S370). Accordingly, the worker is notified of information relating to the presence of the missing components and relating to the missing components.

After the CPU 42 performs the processes of step S360 and step S370, the CPU 42 controls the board processing unit 50 to remove the printed circuit board S from the manufacturing line. The worker performs appropriate processes on the printed circuit board S which is removed from the manufacturing line. For example, when the presence of a foreign object or the position of a foreign object is displayed on the inspection results display screen, the worker performs the re-mounting and the like of the component P which is detected as a missing component using the mounting process device 20 or the like after removing the foreign object from the printed circuit board S based on the position information of the displayed foreign object, and returns the printed circuit board S to the manufacturing line. When the presence of a missing component is displayed and the presence of a foreign object is not displayed on the inspection results display screen, the worker performs remounting or the like of the component P which is detected as a missing component using the mounting process device 20 or the like, and returns the printed circuit board S to the manufacturing line.

According to the mounting inspection device 40 described above, the foreign object inspection on the printed circuit board S is performed on the printed circuit board S on which a missing component of the components P which are mounted is detected based on the results of the missing component inspection. By doing so, when the component P which is a missing component is present on the printed circuit board S, the inspection control unit 41 is capable of detecting the component as a foreign object. Therefore, it is possible to suppress the occurrence of the component P which is a missing component being left on the printed circuit board S, and it is possible to further suppress the occurrence of the printed circuit board S on which the missing component is detected becoming a faulty board. Note that, examples of a case in which the component P which is the missing component is present on the printed circuit board S include a case in which the component P falls onto the printed circuit board S during the conveying to the mounting position, a case in which the component P rebounds due to being pressed too hard onto the printed circuit board S and moves to a position which is shifted from the mounting position, and the like. Since the mounting inspection device 40 does not perform the foreign object inspection on the printed circuit boards S for which a missing component is not detected by the missing component inspection, it is possible to perform the inspection of the printed circuit boards S more efficiently.

The mounting inspection device 40 acquires the missing component position information which is information relating to the positions in which the missing component is detected in the printed circuit board S, and preferentially performs the foreign object inspection on the periphery of the missing component positions which are specified by the missing component position information in the printed circuit board S. The component P which is a missing component has a comparatively high likelihood of being present in the periphery of the correct position of the component P. Therefore, by preferentially performing the foreign object inspection on the periphery of the correct positions of the components P, it is possible to more efficiently detect the components P which is the missing component.

The mounting inspection device 40 acquires the missing component conveying information which is information relating to the conveyance paths over the printed circuit board S when mounting the components P which is the detected missing component, and preferentially performs the foreign object inspection on the regions which are specified by the missing component conveying information in the printed circuit board S. The component P which is a missing component has a comparatively high likelihood of being present in the conveyance path to the correct position of the component P which is detected as a missing component. Therefore, by preferentially performing the foreign object inspection on the region of the printed circuit board S including the conveyance path, it is possible to more efficiently detect the components P which is the missing component.

Furthermore, the mounting inspection device 40 performs the foreign object inspection based on the image processing, acquires the missing component size information which is information relating to the size of the component P which is the missing component, and, based on the acquired missing component size information, performs the foreign object inspection, ignoring foreign objects which are smaller than the component P which is the missing component among the foreign objects which are detected based on the image processing. Therefore, for example, it is possible to further suppress the occurrence of erroneous detection of objects which are smaller than the components P such as solder shifting or the like as foreign objects, and it is possible to more efficiently detect the components P which is the missing component. When there is a plurality of components P which are the missing components, based on the missing component size information of the smallest component P among the components P which are the missing components, the mounting inspection device 40 performs the foreign object inspection, ignoring foreign objects which are smaller than the smallest component P among the foreign objects which are detected based on the image processing. By doing so, when there is a plurality of the components P which are missing components, it is possible to more efficiently detect the component P which is a missing component.

When the printed circuit board S is a multiple printed circuit board, the mounting inspection device 40 performs the foreign object inspection on the child boards in the multiple printed circuit board other than the child boards for which the missing component is detected. Therefore, even when there is a component P which is a missing component on a child board other than the child board for which the missing component is detected, it is possible to detect the component P.

When foreign objects are detected in the foreign object inspection, the mounting inspection device 40 displays the presence of foreign objects on the display section 57. In addition, since the positions of the foreign objects on the printed circuit board S are also displayed, it is possible to efficiently perform the removal of the foreign objects on the printed circuit board S based on the displayed positions.

Note that, the present disclosure is not limited to the embodiment described above, and, needless to say, may be implemented in various modes within the technical scope of the present disclosure.

For example, in the embodiment described above, the mounting inspection device 40 most preferentially performs the foreign object inspection for the foreign object inspection regions including the periphery of a missing component position, and subsequently preferentially performs the foreign object inspection for the foreign object inspection regions including the missing component conveyance paths; however, the disclosure is not limited thereto. For example, the preferential order of the two may be reversed. Alternatively, one or more of the foreign object inspection for the foreign object inspection regions including the periphery of a missing component position and the foreign object inspection for the foreign object inspection regions including the missing component conveyance paths may be omitted.

In the embodiment described above, when there is a plurality of components P which are the missing components, the mounting inspection device 40 sets the threshold Eth based on the missing component size information of the smallest component P among the components P regarding the missing components and performs the foreign object inspection, ignoring foreign objects which are smaller than the smallest component P; however, the disclosure is not limited thereto. For example, the mounting inspection device 40 may set a value which is determined in advance regardless of the missing component size information as the threshold Eth. When there is a plurality of the components P which are missing components, a different threshold Eth may be set for each of the components P. For example, when components P1 and P2 which are the missing components are present, in step S240, the mounting inspection device 40 may perform the foreign object inspection using the threshold Eth1 based on the component P1 for the foreign object inspection region of the periphery of the missing component position of the component P1, and may perform the foreign object inspection using a threshold Eth2 based on the component P2 for the foreign object inspection region of the periphery of the missing component position of the component P2. The same applies to the foreign object inspection in the foreign object inspection region including the missing component conveyance path in step S290.

In the mounting inspection device 40, when there is a plurality of the components P which are the missing components, when a foreign object is detected in the foreign object inspection region which has less than one or more missing components among the plurality of foreign object inspection regions which are set based on the missing component positions or the missing component conveying path, the subsequent foreign object inspection regions may be set based on the information of the components P which are the foreign object inspection regions in which no foreign object is detected. In other words, when the foreign object is detected, following processes may be performed assuming that the component P regarding the foreign object inspection region, in which the foreign object is detected, is detected. For example, when the components P1 and P2 which are missing components are present, in step S240, after the mounting inspection device 40 detects one or more foreign objects in the foreign object inspection region of the periphery of the missing component position of the component P1 and does not detect a foreign object in the foreign object inspection region of the periphery of the missing component position of the component P2, instep S280, the mounting inspection device 40 may set the foreign object inspection region based on the missing component conveyance path of the component P2 and the foreign object inspection region based on the missing component conveyance path of the component P1 may not be set. In this case, the threshold Eth which is used in step S290 may also be set based on the missing component size information of the component P2.

In the embodiment described above, when the printed circuit board S is a multiple printed circuit board, the mounting inspection device 40 performs the foreign object inspection on the child boards in the multiple printed circuit board other than the child boards for which the missing component is detected; however, the disclosure is not limited thereto. For example, the mounting inspection device 40 may perform the foreign object inspection only on the child boards for which the missing component is detected. Alternatively, the mounting inspection device 40 may perform the foreign object inspection only on the child boards for which the missing component is detected and the child boards which are adjacent thereto.

In the embodiment described above, the mounting inspection device 40 displays the presence of foreign objects and the positions of the foreign objects on the printed circuit board S on the display section 57; however, as long as notification is performed, this is not limited to displaying. For example, the mounting inspection device 40 may notify the worker using audio.

In the embodiment described above, the mounting inspection device 40 does not perform the foreign object inspection on the printed circuit boards S in which a missing component is not detected by the missing component inspection; however, the disclosure is not limited thereto. For example, when the test control unit 41 receives input of an execution instruction of the foreign object inspection from the worker via the operation section 58, the foreign object inspection may be performed regardless of the results of the missing component inspection.

In the embodiment described above, the mounting inspection device 40 also uses the captured image data which is acquired in the missing component inspection in the foreign object inspection; however, the captured image data for the foreign object inspection may be acquired separately by the board camera 53.

In the embodiment described above, the printed circuit board S is a multiple printed circuit board including a plurality of child boards; however, the disclosure is not limited thereto, and the printed circuit board S may be a single printed circuit board.

In the embodiment described above, the mounting inspection device 40 performs the missing component inspection and the foreign object inspection by comparing the pre-mounting reference image data or the post-mounting reference image data to the captured image data; however, the disclosure is not limited thereto. For example, pixels which form edges in the captured image data may be detected based on luminance information or the like of each pixel in the captured image data, the outline of the object (the component or the foreign object) may be detected based on the detected edges, and the inspection of the missing component or the inspection of the foreign object may be performed based on the detected object and the mounting condition information 86. The mounting inspection device 40 may perform the missing component inspection or the foreign object inspection by a method other than the image processing.

In the embodiment described above, the component P is sucked by the suction nozzle 34 of the mounting head 33; however, as long as the component P is held by the mounting head 33, the method is not limited to suction. For example, the mounting head 33 may hold the component P by engaging a gripping section with the component P.

In the embodiment described above, the functions of the disclosure are described as the mounting inspection device 40; however, the disclosure is not particularly limited thereto, and may be a mount inspection method or a mode of a program thereof.

INDUSTRIAL APPLICABILITY

It is possible to use the present disclosure in the technical field of mount inspection of inspection a mounting state of a component which is mounted on a printed circuit board.

REFERENCE SIGNS LIST

10: component mounting system, 12: LAN, 20: mounting process device, 21: mounting control unit, 22: CPU, 23: ROM, 24: RAM, 25: HDD, 30: board processing unit, 32: mounting process unit, 33: mounting head, 34: suction nozzle, 35: head moving section, 37: supply unit, 38: part camera, 39: input-output interface, 40: mounting inspection device, 41: inspection control unit, 42: CPU, 43: ROM, 44: RAM, 45: HDD, 50: board processing unit, 52: inspection process unit, 53: board camera, 54: camera moving section, 56: operation panel, 57: display section, 58: operation section, 59: input-output interface, 80: management computer, 81: control device, 82: CPU, 83: ROM, 84: RAM, 85: HDD, 86: mounting condition information, 87: input device, 88: display, 89: input-output interface, P: component, S: printed circuit board

The invention claimed is:

1. A mounting inspection device, comprising:
a board camera that captures an image of a printed circuit board;
missing component inspection circuitry to perform missing component inspection of components mounted on the printed circuit board based on the image of the printed circuit board captured by the board camera and to generate missing component information for specifying the component which has been determined as a missing component; and
foreign object inspection circuitry to perform foreign object inspection in which foreign objects on the printed circuit board are inspected with regard to the printed circuit board on which the missing component has been detected and to not perform the foreign object inspection with regard to the printed circuit board on which the missing component has not been detected, based on the missing component information generated by the missing component inspection circuitry,
wherein the foreign object inspection circuitry specifies a disposition position of the missing component based on the missing component information, the disposition position corresponding to a position in which the missing component is to be mounted, and performs the foreign object inspection by starting on a periphery of the specified disposition position.

2. The mounting inspection device according to claim 1, wherein the foreign object inspection circuitry acquires missing component conveying information which is information relating to a conveyance path over the printed circuit board when mounting a component which is the detected missing component, and performs the foreign object inspection on a region which is specified by the missing component conveying information in the printed circuit board.

3. The mounting inspection device according to claim 1, wherein the foreign object inspection circuitry performs the foreign object inspection based on image processing, acquires missing component size information which is information relating to a size of a component which is the detected missing component, and, based on the acquired missing component size information, performs the foreign object inspection, ignoring foreign objects which are smaller than the component which is the missing component among the foreign objects which are detected based on the image processing.

4. The mounting inspection device according to claim 1, wherein the printed circuit board is a multiple printed circuit board including a plurality of child boards; and wherein, for the multiple printed circuit board on which the missing component is detected by the missing component inspection circuitry, the foreign object inspection circuitry also performs the foreign object inspection on one or more child boards other than the child board on which the missing component is detected in the multiple printed circuit board.

5. A mounting inspection device, comprising:

a board camera that captures an image of a printed circuit board;

missing component inspection circuitry to perform missing component inspection of components mounted on the printed circuit board based on the image of the printed circuit board captured by the board camera and to generate missing component information for specifying the component which has been determined as a missing component; and foreign object inspection circuitry to specify a disposition position of the missing component based on the missing component information generated by the missing component inspection circuitry, the disposition position corresponding to a position in which the missing component is to be mounted, and to perform foreign object inspection in which foreign objects on the printed circuit board are inspected with regard to the printed circuit board on which the missing component has been detected by starting on a periphery of the specified disposition position of the missing component.

* * * * *